United States Patent
Cully et al.

(10) Patent No.: US 9,974,543 B2
(45) Date of Patent: May 22, 2018

(54) ANASTOMOTIC CONNECTORS

(71) Applicant: W. L. Gore & Associates, Inc., Newark, DE (US)

(72) Inventors: Edward H. Cully, Flagstaff, AZ (US); Jeffrey B. Duncan, Flagstaff, AZ (US); James L. Goepfrich, Flagstaff, AZ (US)

(73) Assignee: W. L. Gore & Associates, Inc., Newark (DE)

( * ) Notice: Subject to any disclaimer, the term of this patent is extended or adjusted under 35 U.S.C. 154(b) by 0 days. days.

(21) Appl. No.: 14/558,247

(22) Filed: Dec. 2, 2014

(65) Prior Publication Data

US 2015/0157324 A1  Jun. 11, 2015

Related U.S. Application Data

(60) Provisional application No. 61/912,702, filed on Dec. 6, 2013.

(51) Int. Cl.
| | | |
|---|---|---|
| *A61B 17/08* | (2006.01) | |
| *A61B 17/11* | (2006.01) | |
| *A61F 2/06* | (2013.01) | |
| *A61B 17/00* | (2006.01) | |

(52) U.S. Cl.
CPC ............... *A61B 17/11* (2013.01); *A61F 2/06* (2013.01); *A61F 2/064* (2013.01); *A61B 2017/00004* (2013.01); *A61B 2017/1107* (2013.01); *A61B 2017/1132* (2013.01); *A61B 2017/1135* (2013.01); *A61B 2017/1139* (2013.01); *A61F 2210/0004* (2013.01); *A61F 2250/0039* (2013.01)

(58) Field of Classification Search
CPC ...... A61L 31/148; A61L 29/106; A61B 17/11; A61B 2017/0004; A61B 17/08; A61B 2017/00004; A61B 17/1132; A61B 2017/1135; A61B 2017/1107; A61B 2017/1139; A61F 2/06; A61F 2/064
See application file for complete search history.

(56) References Cited

U.S. PATENT DOCUMENTS

| | | | | |
|---|---|---|---|---|
| 2,428,918 | A | * | 10/1947 | Miller ................. A61B 17/1114 606/154 |
| 3,435,823 | A | | 4/1969 | Edwards |
| 3,683,926 | A | * | 8/1972 | Suzuki .................. A61B 17/11 606/154 |

(Continued)

FOREIGN PATENT DOCUMENTS

| | | |
|---|---|---|
| EP | 716834 | 6/1996 |
| FR | 2 947 716 | 1/2011 |

(Continued)

OTHER PUBLICATIONS

PTFE—Polytetrafluoroethylene—Wikipedia, the free encyclopedia.*

(Continued)

*Primary Examiner* — Victor Nguyen

(57) ABSTRACT

An anastomotic connector includes a tubular shell and a porous biocompatible liner configured to connect two or more natural and/or artificial lumens, such as blood vessels and/or grafts. The tubular shell may be bioabsorbable, ultimately dissolving in the body, while the biocompatible liner can remain in the body and connected to the lumens.

15 Claims, 4 Drawing Sheets

(56) References Cited

U.S. PATENT DOCUMENTS

| | | | |
|---|---|---|---|
| 4,214,586 A | 7/1980 | Mericle | |
| 4,693,249 A | 9/1987 | Schenck et al. | |
| 5,064,057 A | 11/1991 | Iwatsuki et al. | |
| 5,141,516 A | 8/1992 | Detweiler | |
| 5,180,392 A | 1/1993 | Skeie et al. | |
| 5,192,289 A | 3/1993 | Jessen | |
| 5,405,339 A | 4/1995 | Kohnen et al. | |
| 5,527,324 A | 6/1996 | Krantz et al. | |
| 5,669,930 A * | 9/1997 | Igarashi | A61L 31/10 606/191 |
| 5,749,880 A | 5/1998 | Banas et al. | |
| 5,800,522 A * | 9/1998 | Campbell | A61B 17/12022 128/898 |
| 5,989,287 A | 11/1999 | Yang | |
| 6,030,395 A | 2/2000 | Nash et al. | |
| 6,110,188 A * | 8/2000 | Narciso, Jr. | A61B 17/11 606/153 |
| 6,599,302 B2 | 7/2003 | Houser et al. | |
| 6,926,724 B1 | 8/2005 | Chu | |
| 7,011,643 B2 | 3/2006 | Villafana et al. | |
| 2002/0107535 A1 | 8/2002 | Wei et al. | |
| 2004/0073282 A1* | 4/2004 | Stanish | A61B 17/11 623/1.3 |
| 2005/0004584 A1 | 1/2005 | Franco et al. | |
| 2005/0192604 A1* | 9/2005 | Carson | A61B 17/11 606/153 |
| 2007/0179599 A1 | 8/2007 | Brodbeck et al. | |
| 2007/0270932 A1* | 11/2007 | Headley | A61F 2/95 623/1.11 |
| 2008/0167595 A1 | 7/2008 | Porter et al. | |
| 2010/0145438 A1* | 6/2010 | Barone | A61F 2/2418 623/2.1 |
| 2011/0098732 A1* | 4/2011 | Jacobs | A61B 17/0643 606/153 |
| 2013/0110141 A1* | 5/2013 | Chmura | A61B 17/1114 606/153 |
| 2015/0157324 A1* | 6/2015 | Cully | A61B 17/11 606/153 |

FOREIGN PATENT DOCUMENTS

| | | |
|---|---|---|
| JP | 2004-275338 | 10/2004 |
| WO | 03/094797 | 11/2003 |
| WO | 2005/065578 | 7/2005 |
| WO | 2013/065040 | 5/2013 |

OTHER PUBLICATIONS

International Search Report and Written Opinion for PCT/US2014/068425 dated Feb. 12, 2015, corresponding to U.S. Appl. No. 14/558,247, 5 pages.

* cited by examiner

ANASTOMOTIC CONNECTORS

TECHNICAL FIELD

This document relates to anastomotic connectors that may be used for providing connections between natural and/or artificial lumens within a patient.

BACKGROUND

Medical devices are frequently used to treat the anatomy of patients. Such devices can be permanently or semi-permanently implanted in the anatomy to provide treatment to a patient. Frequently, these devices, including stents, grafts, stent-grafts, anastomotic connectors, filters, valves, occluders, markers, mapping devices, therapeutic agent delivery devices, prostheses, pumps, bandages, and other endoluminal and implantable devices, are inserted into the body at an insertion point and delivered to a treatment site using a catheter.

Anastomotic connectors can be used to join natural lumens, such as blood vessels, and/or artificial lumens, such as grafts and stent-grafts. Such devices can, for example, assist in the repair or replacement of blood vessels.

The use of anastomotic connectors can pose potential issues. Such complications can be reduced or alleviated by providing an anastomotic connector that is implanted in the body of the patient and can dissolve or degrade after a set period of time.

SUMMARY

In a first general aspect, an anastomotic connector of the present disclosure includes a bioabsorbable tubular shell and a porous polymeric liner. The porous polymeric liner, covers, at least in part, the bioabsorbable tubular shell. After the bioabsorbable tubular shell has been absorbed into the body of the patient, the porous polymeric liner is left behind in the patient, and is capable of maintaining a lumen for fluid flow.

In another aspect, the tubular shell is made from an implantable material that is not bioabsorbable. In this aspect, the porous polymeric liner, also surrounds, at least in part, the tubular shell.

The details of one or more embodiments are set forth in the accompanying drawings and the description below. Other features, objects, and advantages will be apparent from the description and the drawings, and from the claims.

Figure 1:
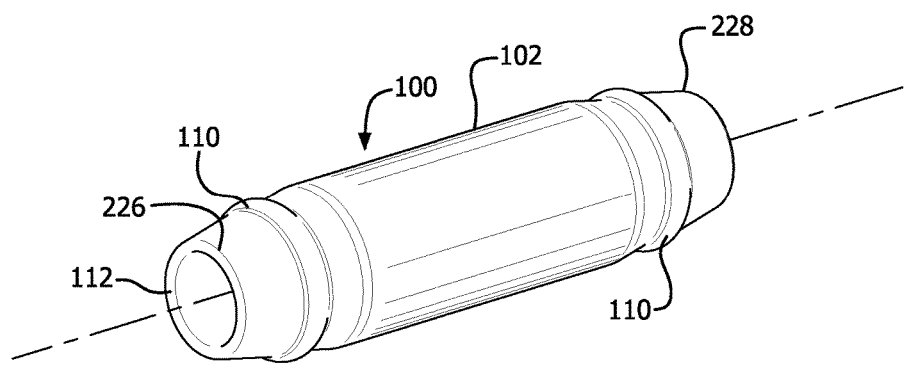
FIG. 1 is a perspective view of an anastomotic connector in accordance with the present disclosure.

Like reference symbols in the various drawings indicate like elements. It should also be noted that the accompanying drawing figures referred to herein are not all drawn to scale, but may be exaggerated to illustrate various aspects of the present disclosure, and in that regard, the drawing figures should not be construed as limiting.

DETAILED DESCRIPTION OF THE ILLUSTRATED EMBODIMENTS

This document describes devices, systems, and methods that are useful, for example, for repairing, supporting, and/or replacing anatomical lumens. Several implantable medical devices are described herein, and in general any of the features described with respect to a particular device may also be used with any of the other devices described herein. In some examples, one or more features described with respect to a particular device may be added to or included with another device. Also, various combinations or sub-combinations of any of the features described herein may generally be used with any of the devices described herein.

In general, any of the implantable medical devices described herein can be delivered to, and deployed at, an in vivo deployment site within a body of a patient using various minimally invasive transcatheter deployment techniques. For example, any of the implantable medical devices described herein may be releasably attached to a delivery catheter. Further, any of the implantable devices described herein can be delivered to, and deployed at, an in vivo deployment site within a body of a patient using variously minimally invasive surgical techniques. Likewise, these devices may also be surgically implanted via vascular surgical techniques.

Any of the anastomotic connectors discussed herein can be used to repair and/or connect natural and/or artificial lumens. In various embodiments, anastomotic connectors of the present disclosure can be used in a body lumen, including those within the circulatory and gastrointestinal systems.

As used herein, "implantable" means implanted in the body of a patient for more than 29 days.

As used herein, "bioabsorbable" means resorbable, dissolvable, absorbable, degradable, erodible, or the like, whether over time and/or upon activation by an external stimulus (e.g., liquid, heat, light, etc.).

With reference to FIG. 1, an example anastomotic connector 100 comprises a tubular shell 102 (optionally bioabsorbable) and a liner 112. Anastomotic connector 100 can be implanted in the body of a patient to connect two or more natural and/or artificial lumens. For example, anastomotic connector 100 can connect two blood vessels, a blood vessel and a vascular graft or stent-graft, two vascular grafts or two stent-grafts. Further, bioabsorbable tubular shell 102 of anastomotic connector 100 can dissolve in the body of the patient, leaving behind liner 112 between the two natural and/or artificial lumens.

In various embodiments, the tubular shell 102 comprises a biocompatible material that may be polymeric (e.g., PTFE or nylon) or metallic (e.g., stainless steel or nitinol).

In various embodiments, bioabsorbable tubular shell 102 comprises a bioabsorbable material capable of being absorbed by the body of a patient. For example, bioabsorbable tubular shell 102 can comprise a metallic material, such as magnesium. Bioabsorbable tubular shell 102 can also comprise a polymeric bioabsorbable material, such as a polyglycolide and trimethylene carbonate copolymer. Although described in connection with particular materials, the use of any bioabsorbable material for bioabsorbable tubular shell 102 is within the scope of the present disclosure.

Bioabsorbable tubular shell 102 comprises a luminal surface 104 and an abluminal surface 106. In various embodiments, liner 112 is positioned within shell 102 such that liner 112 covers luminal surface 104 of tubular shell 102. Liner 112 can also cover at least a portion of abluminal surface 106, such as at the ends of the tubular shell 102.

Figure 2A:
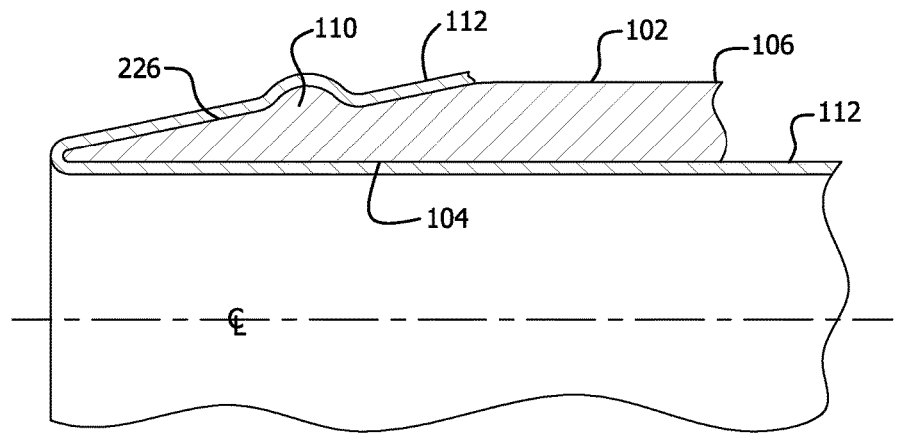
FIGS. 2A and 2B are longitudinal cross sectional views of an end portion of two anastomotic connectors in accordance with the present disclosure.
Figure 2B:
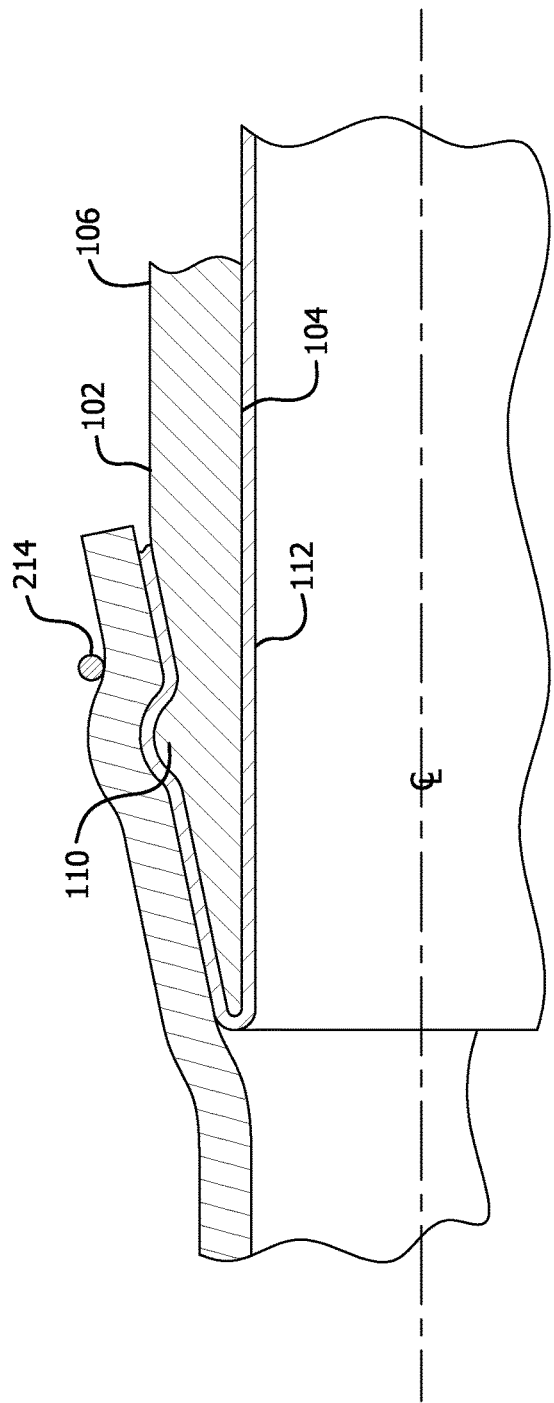

With reference to FIGS. 1, 2A and 2B, bioabsorbable tubular shell 102 comprises a first end 226 and a second end 228. One or more retention means 110 can be positioned one or more ends of bioabsorbable tubular shell 102. Retention means 110 can comprise, for example, a region of increased thickness or diameter, such as a barb, bump, flare, or angled segment. In such embodiments, retention means 110 can assist in securing anastomotic connector 100 to a natural and/or artificial lumen by providing a pressure fit within the lumen. In various embodiments, liner 112 can extend outward from one or more ends and fold over one or more of retaining members 110.

In various embodiments, anastomotic connector 100 can further comprise one or more external retention members 214. For example, external retention members 214 can be located at or near one or more ends of bioabsorbable tubular shell 102. External retention members 214 can engage the natural (i.e., blood vessel) and/or artificial lumen (i.e., graft) to provide pressure to maintain the position of anastomotic connector 100 relative to the lumen. In various embodiments, external retention members 214 comprise one of a suture, an o-ring, and a clip. Any external retention member capable of engaging with a natural and/or artificial lumen and assist in maintaining a desired position of anastomotic connector is within the scope of the present disclosure.

With reference back to FIG. 1, liner 112 can comprise, for example, a porous polymeric material. For example, liner 112 can comprise an ePTFE tubular member, such as a longitudinally extruded and longitudinally expanded ePTFE tube or an ePTFE tube comprising an ePTFE film (typically formed by wrapping such a film over the surface of a mandrel). In general, liner 112 can comprise any porous polymeric biocompatible material, such as an expanded polymer, including expanded polytetrafluoroethylene ("ePTFE"), expanded modified PTFE, expanded copolymers of PTFE, nylons, polycarbonates, polyethylenes, polypropylenes, polyurethanes and the like.

In various embodiments, as bioabsorbable tubular shell 102 dissolves, tissue can ingrow into liner 112. In such embodiments, liner 112 remains in the body and maintains connection and a luminal pathway between the at least two natural and/or artificial lumens.

Liner 112 can comprise, for example, an ePTFE material that is distensible. In various embodiments, liner 112 comprises a material that can be made distensible after implantation of anastomotic connector 100. For example, a balloon can manipulate anastomotic connector 100 to expand and/or lengthwise extend liner 112 after implantation. Such distension can occur after bioabsorbable tubular shell 102 dissolves sufficiently to allow liner 112 to change in dimension or configuration.

In various embodiments, liner 112 can be coated with a biocompatible coating such as for example, a therapeutic agent. For example, liner 112 can be coated with heparin. In such configurations, blood can flow through anastomotic connector 100 and be exposed to the coating of liner 112.

Figure 3A:
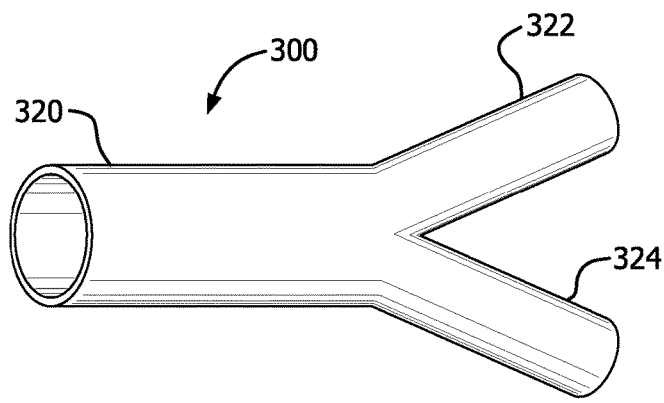
FIGS. 3A-3C are side views of various anastomotic connectors in accordance with the present disclosure.
Figure 3B:
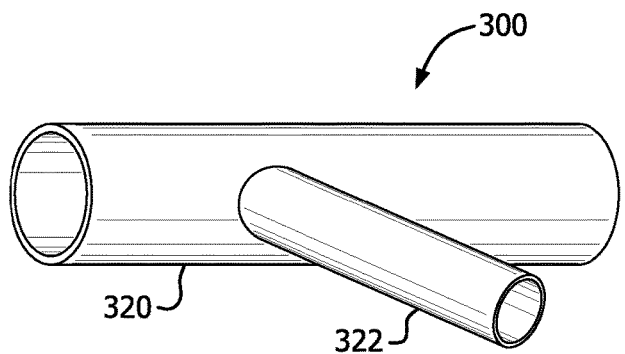

With reference now to FIGS. 3A-3B, various configurations of anastomotic connector 300 are illustrated. For example, with reference to FIG. 3A, an example anastomotic connector 300 illustrated in FIG. 3A comprises a bifurcated configuration, having a main body 320, a first branch 322 and a second branch 324. With reference to FIG. 3B, another example anastomotic connector 300 can comprise a branched configuration, having a main body 320 and a first branch 322.

Figure 3C:
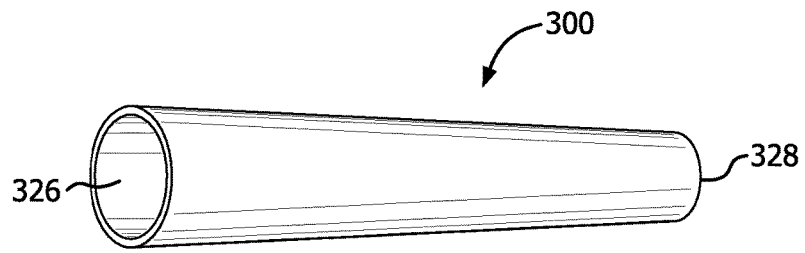

With reference to FIG. 3C, yet another example anastomotic connector 300 can comprise a first end 326 and a second end 328. In various embodiments, first end 326 and second end 328 comprise circular cross sections of different diameters. In such embodiments, anastomotic connector 300 comprises a tapered segment which tapers from the diameter of first end 326 to the diameter of second end 328, or vice versa.

Figure 4A:
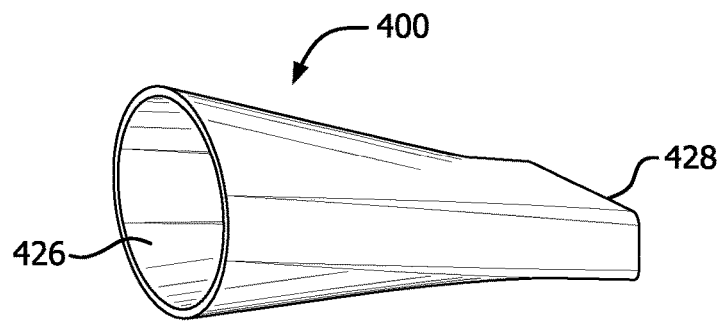
FIGS. 4A and 4B are a perspective view and an end view, respectively, of another anastomotic connector in accordance with the present disclosure.
Figure 4B:
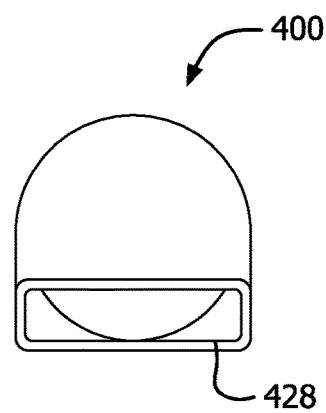

In various embodiments, with reference to FIGS. 4A and 4B, an example anastomotic connector 400 can comprise a first end 426 and second end 428. First end 426 and second end 428 can comprise different profiles. For example, first end 426 can comprise a circular cross section, and second end 428 can comprise a non-circular cross section such as, for example, an elliptical shape (e.g., circles, ovals, ellipses, and the like), a non-elliptical shape (e.g., triangles, rectangles, squares, hexagons, trapezoids, pentagons, stars, and the like), or a random shape. However, the use of a biocompatible tubular shell having any cross sectional shape is within the scope of the present disclosure.

Any portion of an anastomotic connector as described herein can comprise a therapeutic agent, for example, be coated or imbibed with a therapeutic agent, whether dry, gel or liquid. Examples of therapeutic agents comprise antiproliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP)IIbIIIa inhibitors and vitronectin receptor antagonists; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine{cladribine}); platinum coordination complexes (cisplatin, carboplatin), procarbazine, hydroxyurea, mitotane, aminoglutethimide; hormones (i.e. estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF) platelet derived growth factor (PDGF), erythropoetin; angiotensin receptor blocker; nitric oxide donors; anti-sense oligionucleotides and combinations thereof; cell cycle inhibitors, mTOR inhibitors, growth factor signal transduction kinase inhibitors, chemical compound, biological molecule, nucleic acids such as DNA and RNA, amino acids, peptide, protein or combinations thereof.

Several characteristics and advantages have been set forth in the preceding description, including various alternatives together with details of the structure and function of the devices and methods. The disclosure is intended as illustrative only and as such is not intended to be exhaustive or limiting. It will be evident to those skilled in the art that various modifications may be made, especially in matters of structure, materials, elements, components, shapes, sizes, and arrangements of parts including combinations within the principles described herein, to the full extent indicated by the broad, general meaning of the terms in which the appended claims are expressed. To the extent that these various modifications depart from the spirit and scope of the appended claims, they are intended to be encompassed therein. All references, publications, and patents referred to herein, including the figures and drawings included therewith, are incorporated by reference in their entirety.

What is claimed is:

1. An anastomotic connector comprising:
   a tubular shell comprising a wall defining an abluminal surface, a luminal surface, and two ends, at least one of the two ends comprising a liner retention means formed by a portion of the wall of the tubular shell that has an increased thickness between the luminal surface and abluminal surface of the wall relative to a thickness of the wall between the luminal and abluminal surface of adjacent portions of the wall of the tubular shell, the wall of the tubular shell comprising a bioabsorbable material;
   a liner that is porous, polymeric, biocompatible, and non-bioabsorbable such that the liner remains in the body after bioabsorption of the tubular shell, wherein the liner covers at least the luminal surface of the tubular shell; and
   an external retention member configured to be located proximate the liner retention means and to provide pressure between the liner retention means and a natural and/or artificial lumen to which the anastomotic connector is connected to maintain a position of the anastomotic connector relative to natural and/or artificial lumen; wherein the portion of the tubular shell forming the liner retention means has an increased diameter relative to the adjacent portions of the tubular shell.

2. The anastomotic connector according to claim 1, wherein the liner retention means includes a barb, bump, flare, or angled segment.

3. The anastomotic connector according to claim 1, wherein the liner retention means is a retention means for assisting in securing anastomotic connector to the natural and/or artificial lumen by providing a pressure fit within the lumen.

4. The anastomotic connector according to claim 1, wherein the liner extends outward from the at least one of the two ends comprising the liner retention means and folds over the liner retention means.

5. The anastomotic connector according to claim 1, further comprising one or more external retention members configured to engage a natural and/or artificial lumen.

6. The anastomotic connector according to claim 5, wherein the one or more external retention members includes a suture, an O-ring, or a clip.

7. The anastomotic connector according to claim 1, wherein the liner comprises an expanded PTFE tubular member.

8. The anastomotic connector according to claim 1, wherein the liner is configured to be expanded by balloon dilation after the bioabsorbable material of the tubular shell dissolves.

9. An anastomotic connector comprising:
   a tubular shell having a wall that is bioabsorbable and comprises a bioabsorbable material and defines an abluminal surface, a luminal surface, and two ends, at least one of the two ends comprising a liner retention means formed by a thicker part of the wall of the tubular shell that has an increased thickness relative to adjacent portions of the wall of the tubular shell;
   a porous polymeric biocompatible liner that is non-bioabsorbable, wherein the porous polymeric biocompatible liner covers at least the luminal surface of the tubular shell and the liner extends outward from the at least one of the two ends comprising the liner retention means and folds over the liner retention means; and
   an external retention member configured to be located proximate the liner retention means and to provide pressure between the liner retention means and a natural and/or artificial lumen to which the anastomotic connector is connected to maintain a position of the anastomotic connector relative to natural and/or artificial lumen; wherein the liner retention means is formed by a region of the tubular shell having an increased diameter.

10. The anastomotic connector according to claim 9, wherein the liner retention means is a barb, bump, flare, or angled segment.

11. The anastomotic connector according to claim 9, wherein the liner retention means is a retention means for assisting in securing anastomotic connector to a natural and/or artificial lumen by providing a pressure fit within the lumen.

12. The anastomotic connector according to claim 9, further comprising one or more external retention members configured to engage a natural and/or artificial lumen.

13. The anastomotic connector according to claim 12, wherein the one or more external retention members includes a suture, an O-ring, or a clip.

14. The anastomotic connector according to claim 9, wherein the liner is configured to be expanded by balloon dilation after the bioabsorbable material of the tubular shell dissolves.

15. The anastomotic connector according to claim 9, wherein the liner comprises an expanded PTFE tubular member.

* * * * *